US009659229B2

(12) United States Patent
Clifton et al.

(10) Patent No.: US 9,659,229 B2
(45) Date of Patent: May 23, 2017

(54) METHOD AND SYSTEM FOR SIGNAL ANALYSIS

(71) Applicant: ISIS INNOVATION LIMITED, Oxford, Oxfordshire (GB)

(72) Inventors: David Andrew Clifton, Oxford (GB); Mauricio Christian Villarroel Montoya, Oxford (GB); Lionel Tarassenko, Oxford (GB)

(73) Assignee: ISIS INNOVATION LIMITED, Oxford, Oxfordshire (GB)

( * ) Notice: Subject to any disclaimer, the term of this patent is extended or adjusted under 35 U.S.C. 154(b) by 16 days.

(21) Appl. No.: 14/767,507

(22) PCT Filed: Jan. 28, 2014

(86) PCT No.: PCT/GB2014/050211
§ 371 (c)(1),
(2) Date: Aug. 12, 2015

(87) PCT Pub. No.: WO2014/125250
PCT Pub. Date: Aug. 21, 2014

(65) Prior Publication Data
US 2015/0379370 A1 Dec. 31, 2015

(30) Foreign Application Priority Data
Feb. 12, 2013 (GB) .................................. 1302451.8

(51) Int. Cl.
*G06K 9/46* (2006.01)
*A61B 5/0205* (2006.01)
(Continued)

(52) U.S. Cl.
CPC .......... *G06K 9/4661* (2013.01); *A61B 5/0013* (2013.01); *A61B 5/0022* (2013.01);
(Continued)

(58) Field of Classification Search
CPC ... G06T 7/0012; G06T 7/0079; G06T 7/0097; G06T 7/20; G06T 7/408;
(Continued)

(56) References Cited

U.S. PATENT DOCUMENTS

| 2010/0298730 A1 | 11/2010 | Tarassenko et al. .......... 600/529 |
| 2013/0197383 A1 | 8/2013 | Chon et al. .......... A61B 5/0816 |
| 2014/0303454 A1 | 10/2014 | Clifton et al. ....... A61B 5/7203 |

FOREIGN PATENT DOCUMENTS

| WO | WO-2009/016334 A1 | 2/2009 | ............. A61B 5/024 |
| WO | WO-2012/051295 A2 | 4/2012 | ............... A61B 5/08 |
| WO | WO-2013/027027 A2 | 2/2013 | ........... A61B 5/0205 |

OTHER PUBLICATIONS

International Preliminary Report on Patentability,CH. I, IB, Geneva, issued Aug. 18, 2015.
(Continued)

*Primary Examiner* — Andrew W Johns
(74) *Attorney, Agent, or Firm* — Harness, Dickey & Pierce, P.L.C.

(57) ABSTRACT

An image of a human, animal or machine subject, is analysed to detect regions which include strong periodic intensity variations, such as a photoplethysmogram (PPG) signal in a human or animal, or some periodic vibration in a machine. The image is divided into plural regions of fixed order is fitted to a representative intensity signal for that region. The poles of the fitted autoregressive model are thresholded by magnitude to select only the pole or poles with a magnitude greater than the threshold. The pole magnitude therefore acts as a signal quality index. The dominant pole is representative of the strongest periodic information and the frequency of that spectral component can be derived from the phase angle of the pole. The image may be redisplayed with image attributes, e.g. color-coding, according to the pole magnitude in each region of interest
(Continued)

and/or the dominant pole phase angle in each region of interest. In the case of a PPG image signal this can give maps of heart rate and breathing rate.

19 Claims, 4 Drawing Sheets

(51) Int. Cl.
    *A61B 5/024*     (2006.01)
    *G06T 7/00*     (2017.01)
    *A61B 5/00*     (2006.01)
    *G06T 11/00*     (2006.01)
    *G06T 11/20*     (2006.01)
    *G06T 7/10*     (2017.01)
    *G06T 7/90*     (2017.01)
    *A61B 5/08*     (2006.01)
    *A61B 5/1455*     (2006.01)

(52) U.S. Cl.
    CPC .......... *A61B 5/0075* (2013.01); *A61B 5/0077* (2013.01); *A61B 5/0205* (2013.01); *A61B 5/02416* (2013.01); *A61B 5/7221* (2013.01); *A61B 5/743* (2013.01); *G06K 9/46* (2013.01); *G06K 9/4652* (2013.01); *G06T 7/0012* (2013.01); *G06T 7/10* (2017.01); *G06T 7/90* (2017.01); *G06T 11/001* (2013.01); *G06T 11/206* (2013.01); *A61B 5/02427* (2013.01); *A61B 5/0816* (2013.01); *A61B 5/14551* (2013.01); *A61B 2503/40* (2013.01); *A61B 2576/00* (2013.01); *G06K 2009/4666* (2013.01); *G06T 2207/10016* (2013.01); *G06T 2207/10024* (2013.01); *G06T 2207/20021* (2013.01); *G06T 2207/30076* (2013.01); *G06T 2207/30088* (2013.01); *G06T 2207/30104* (2013.01); *G06T 2207/30201* (2013.01)

(58) Field of Classification Search
    CPC ........ G06T 2207/20021; G06K 9/4652; G06K 9/4661; A61B 5/0075; A61B 5/0205; A61B 5/02416; A61B 5/0816; A61B 5/1455; A61B 5/7221; A61B 2576/00
    See application file for complete search history.

(56) References Cited

OTHER PUBLICATIONS

Yu Sun et al.: "Motion-compensated noncontact imaging photoplethysmography to monitor cardiorespiratory status during exercise," Journal of Biomedical Optics, vol. 16, No. 7, Jan. 1, 2011 (Jan. 1, 2011), p. 077010, XP055017559, ISSN: 1083-3668, DOI: 10.1117/1.3602852.

International Search Report and Written Opinion of the ISA, ISA/EP, Rijswijk, NL, mailed Mar. 28, 2014.

UK Search Report under Section 17(5) for priority application GB 1302451.8, issued Jul. 31, 2013.

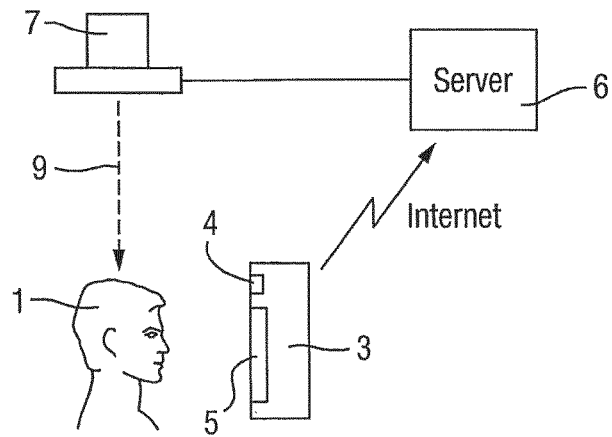
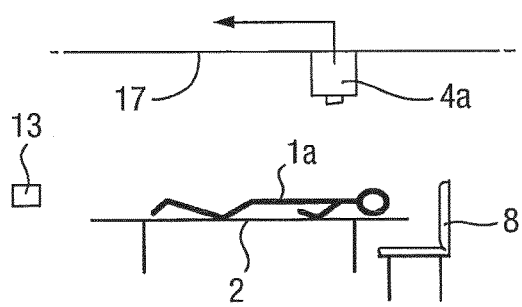
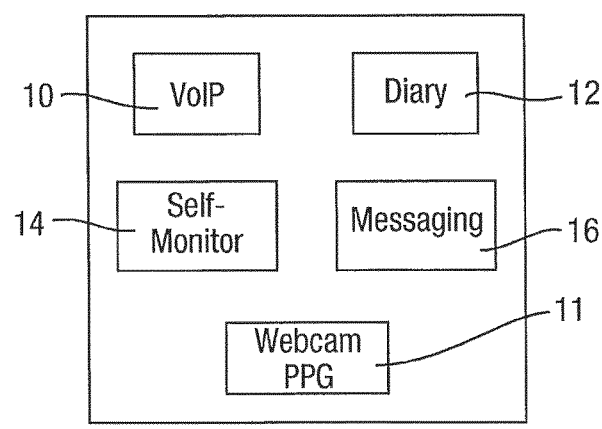

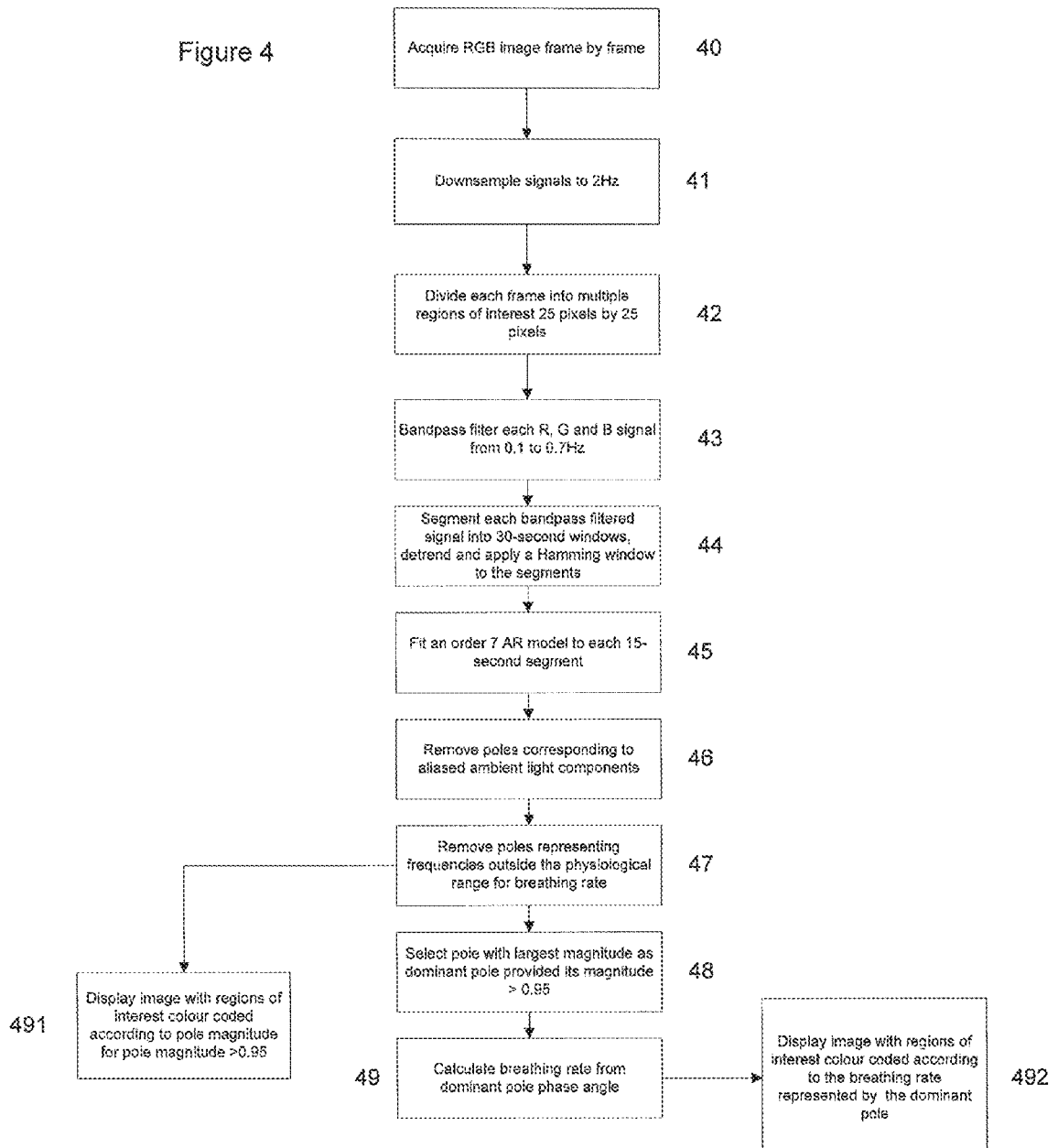

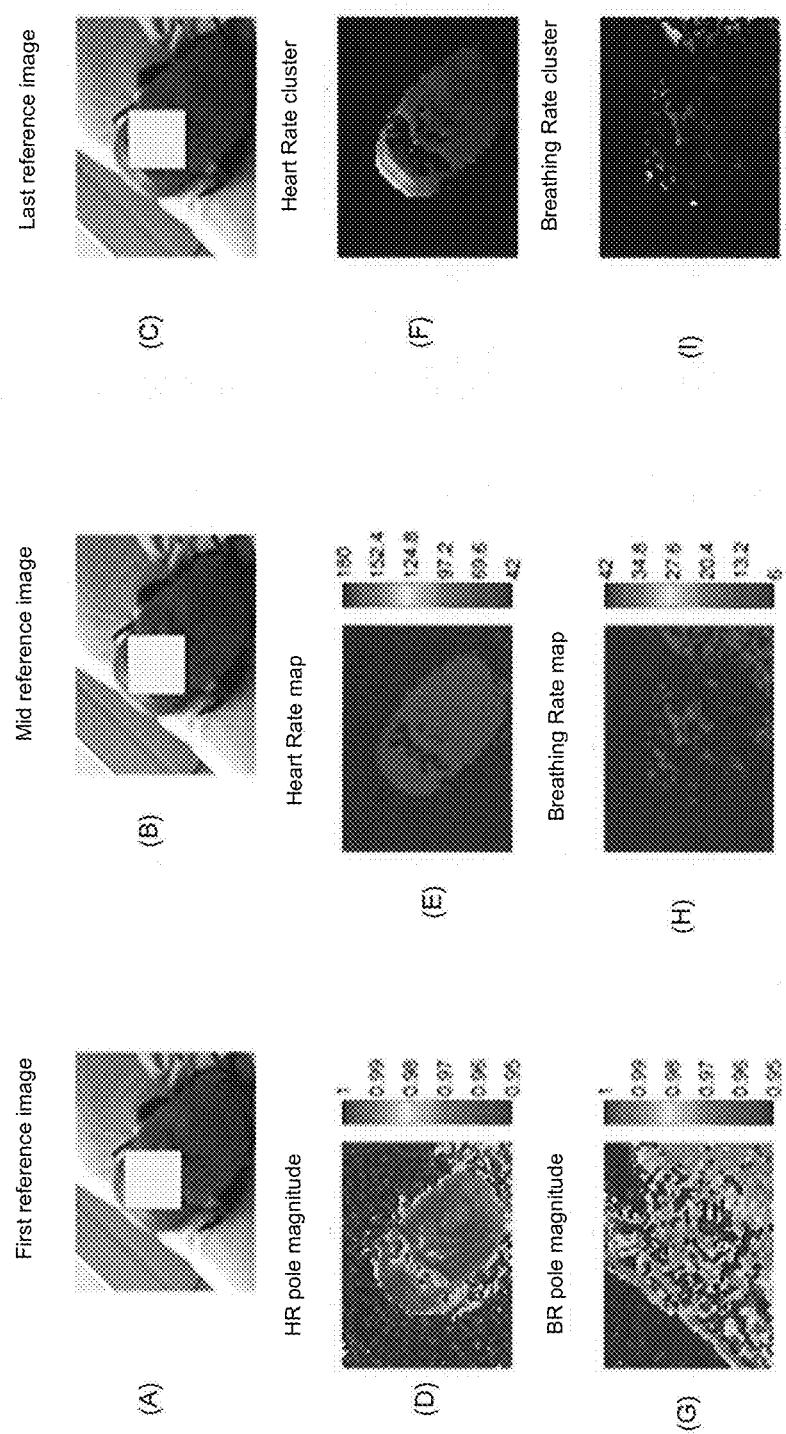

METHOD AND SYSTEM FOR SIGNAL ANALYSIS

CROSS REFERENCE TO RELATED APPLICATIONS

This application is a 371 U.S. National Stage of International Application No. PCT/GB2014/050211, filed Jan. 28, 2014. This application claims the benefit of and priority to British Patent Application No. 1302451.8, filed Feb. 12, 2013. The entire disclosures of each of the above applications are incorporated herein by reference.

The present invention relates to a method and a system for signal analysis, in particular for detecting periodic information in signals and to a signal quality indicator indicative of the degree of confidence that the periodic information is valid.

There are a broad range of fields in which signals representative of measurements on a system are analysed to detect periodic information representing some state of the system. For example in the medical field a human or animal subject's vital sign include heart rate and breathing rate which are types of periodic information indicative of the state of the subject. In the engineering field, machinery, particularly machinery including rotating components, can be monitored by vibration or acoustic sensors and the presence or absence of sounds or vibrations at particular frequencies can be indicative of normal or abnormal operation. In both the medical and engineering fields, however, measured signals tend to be noisy and it can be difficult for automated analysis systems to determine whether a signal being measured is carrying information which is valid, i.e. truly representative of the system state being measured. Even when signals are spectrally analysed to detect the dominant frequencies within them, it can be difficult to distinguish between artifact and true signals and automated analysis may be confused by noise and signal dropout.

The present invention provides a method of analyzing a signal to detect periodic information carried by it whilst also providing a signal quality indicator indicating the degree of confidence that the detected information is valid. The invention also provides a signal analysis system executing such a method.

In more detail the present invention utilizes an autoregressive model, preferably all-pole fixed-order model, to analyses the signal. If the signal to be analysed is expected to have one dominant frequency (for example, the cardiac frequency), then the magnitude of the dominant pole, typically the pole with the highest magnitude (largest radius), in the fitted autoregressive model is taken as an indicator of signal quality. Thus, for example, a threshold can be applied to the pole magnitude (i.e. pole radius on the pole-zero plot) and only if the pole magnitude exceeds the threshold is the spectral component represented by that pole regarded as valid. The frequency of the spectral component corresponding to a valid pole can be calculated from the phase angle of the pole and thus can be taken to represent valid information about the system being monitored.

The invention may be applied to simple signals (i.e. one dimension plus time) such as acoustic or vibration signals, or transmittance or reflectance signals from a photoplethysmogram probe (which measures transmittance or reflectance on the finger or the ear). In the case of a photoplethysmogram (PPG) signal this can allow the derivation of heart rate from the signal.

However, the invention is particularly useful in analyzing more complex signals, such as image signals which contain periodic intensity variations representing temporal information about the imaged subject. It finds particular application in the analysis of photoplethysmogram image signals in which an image of the subject's face or body is analysed to derive the PPG signal, and from it heart rate, breathing rate or blood oxygen saturation ($SpO_2$).

To explain photoplethysmography in more detail, it has been well known since the 1930s—see the introduction in the paper by Verkruysse W, Svaasand L O and Nelson J S entitled "Remote plethysmographic imaging using ambient light", *Optics Express*, 2008, 16(26), 21434-45—that the variations in blood volume in a body segment with each heart beat modulate the transmission of visible (or infra-red) light through, or the reflection from, that body segment. Blood absorbs visible and infra-red light more than the surrounding tissue in the body segment, hence the variations in blood volume during the cardiac cycle affect the transmission or reflectance of light in time with the heart beat. The cardiac-synchronous variations in light transmission or reflectance are known as the photoplethysmographic (PPG) signal. The heart rate (or pulse rate—the two are equivalent) can easily be extracted from the PPG signal by measuring the time interval between two consecutive peaks (or troughs) of the PPG waveform. The respiratory (or breathing) rate can also be estimated indirectly from relatively complex analysis of the PPG waveform, (for example, by measuring the changes in inter-beat interval which occur over the respiratory cycle or by measuring the breathing-rate-synchronous amplitude modulation of the PPG signal).

In the 1970s, the technique of pulse oximetry was developed to obtain a non-invasive estimate of peripheral arterial oxygen saturation ($SpO_2$) by measuring the PPG signal at two wavelengths. The two common forms of the hemoglobin molecule (the oxygen carrier in the blood), oxidised hemoglobin ($HbO_2$) and reduced hemoglobin (Hb), have significantly different optical spectra in the wavelength range from 500 nm to 1000 nm. Hence, by measuring the light transmitted through the fingertip (or the earlobe) at two different wavelengths using a simple probe with two light-emitting diodes, one in the red and the other in the near infra-red, pulse oximeters determine the oxygen saturation of the arterial blood in the finger (or ear) non-invasively.

The possibility of measuring PPG signals remotely using a camera (rather than a probe attached to the finger, ear or toe) is first discussed in the scientific literature around 2005 (see Wieringa F P, Mastik F and Van Der Steen A F W, Contactless Multiple Wavelength Photoplethysmographic Imaging: A First Step Toward "$SpO_2$ Camera" Technology, *Annals of Biomedical Engineering*, 2005, 33(8), 1034-1041 and Humphreys K, Ward T, Markham C, Noncontact simultaneous dual wavelength photoplethysmography: A further step toward noncontact pulse oximetry, *Rev. Sci. Instrum.*, 2007, 78, 044304). In the 2008 paper from Verkruysse, Svaasand and Nelson mentioned above, the authors show that PPG signals can be remotely acquired from the human face with normal ambient light as the source and a simple, digital, consumer-level camera as the detector more than 1 m away. Regions of interest (usually the forehead) were selected in images of the faces of human volunteers. The paper shows how heart rate can be extracted from the frequency content of these images (using the Fast Fourier Transform for 10-sec windows), and hints at how breathing rate may be computed. They suggest that the main application of this remote sensing technology might be in triage and sports.

More recently, there have been two papers published by a team from the Affective Computing group in the MIT Media Lab. (see Poh MZ, McDuff DJ, Picard RW, Non-contact, automated cardiac pulse measurements using video imaging and blind source separation, *Optics Express,* 2010, 18, 10762-10744 and Poh MZ, McDuff DJ, Picard RW, Advancements in noncontact, multi-parameter physiological measurements using a webcam, *IEEE Trans Biomed Eng.,* 2011, 58, 7-11). The team have recorded videos of facial regions with a webcam. They focus on sources of fluctuations in light due to artefacts caused by motion and changes in ambient light conditions. Although their experiments were carried out indoors, the only source of illumination was a varying amount of ambient sunlight entering through windows.

There are various problems with making PPG imaging work in real-world settings. One example is the interference caused by the aliasing of the artificial light, e.g. fluorescent light, found in most indoor environments outside daylight hours and often within daylight hours as well. Although the 50 Hz frequency of artificial light is much higher than the physiological signals (heart rate or breathing rate) to be measured, in practice the sampling process in the camera aliases the 50 Hz components down to much lower frequencies. Aliasing components are often found at frequencies such as 4 Hz and 2 Hz which are in the physiological range. Also subjects may move, creating an artifact, and there may be other sources of periodic signal in the field of view of the camera.

The present invention provides a particularly effective way of analyzing such image signals to derive the periodic information in them and to indicate which areas of the image contain periodic intensity variations representing valid temporal information about the subject. This is achieved by dividing the image into plural spatial areas or regions of interest, fitting an autoregressive model to a representative intensity signal from each region of interest and assessing the magnitude of the dominant pole (typically the pole with the highest magnitude) for each region against a threshold. If the magnitude of the dominant pole is greater than the threshold then the spectral component represented by that pole is regarded as carrying valid temporal information.

In more detail the present invention provides a method of analyzing an image of a subject to identify spatial areas which contain periodic intensity variations representing valid temporal information about the subject, comprising the steps of dividing said image into a plurality of spatial areas and obtaining respective signals representative of an image intensity for each spatial area; spectrally analyzing the intensity variations of each representative signal by fitting respective autoregressive models to the representative signals, each of the fitted autoregressive models comprising a plurality of poles representing spectral components of the intensity variations of each representative signal, each pole having a magnitude dependent upon the strength of the spectral component and a phase angle dependent upon the frequency of the spectral component; selecting those spatial areas whose fitted autoregressive model has a pole whose magnitude is greater than a predetermined threshold and identifying those spatial areas as containing periodic intensity variations representing said valid temporal information. The pole magnitude is effectively being used as a signal quality index (SQI).

The spatial areas are preferably defined as m by n pixels of the image where m and n are positive integers. Typically areas of 25 by 25 pixels may be used, though each spatial area may be one pixel (m=n=1) or more than 25 by 25 as appropriate.

Where the spatial areas each contain more than one pixel the representative signal can be an average or modal intensity over the spatial area.

The image is preferably a three colour component image such as an RGB image and the method may be applied to one, two or all three of the colour components in each area. The colour component chosen to derive the physiological information (typically the heart rate or the breathing rate) is usually the green colour, but the choice of colour component may also be made by selecting that colour for which the magnitude of the dominant pole is the highest. Alternatively, the phase angle for the dominant pole may be computed for each colour and the median value chosen to estimate the periodic frequency of interest.

The threshold on pole magnitude to be regarded as carrying valid information is set empirically as appropriate for the application. The value of the threshold will depend on the size of the Region of Interest. For a small region, for example 25×25 pixels, the threshold may be as high as 0.99. For a larger region, for example 250×250 pixels, the value of the threshold may be lower. The threshold can be adaptive, and can vary from patient to patient.

Preferably knowledge of the expected frequency range for the temporal information is used to identify and ignore poles representing spectral components outside that range. For example in the case of heart rate detection frequencies outside the range 0.7 Hz to 4 Hz, corresponding to 42 to 240 beats/min, can be ignored. In the case of breathing rate frequencies outside the range 0.1 Hz to 0.7 Hz, corresponding to 6 to 42 breaths/min can be ignored.

It is also possible to identify and ignore poles representing spectral components from ambient light interference caused by aliasing by comparing the poles present in a model fitted to an image signal from the subject with poles present in a model fitted to an image signal from elsewhere in the image, for example background. Poles with the same phase angle (to within a given tolerance, typically 1°) in both are clearly not representing information from the subject and so can be eliminated.

Preferably, for each spatial area, a dominant pole is selected. For the estimation of heart rate, the dominant pole is the pole with the highest magnitude. For the estimation of breathing rate, the dominant pole is the pole of smallest phase angle (lowest frequency) whose magnitude is at least 0.95 of the magnitude of the highest-magnitude pole.

An additional check may be made to validate the choice of dominant pole. The frequency spectrum of the windowed signal may be determined using either the standard Discrete Fourier Transform (or Fast Fourier Transform) or by evaluating $H(z=e^{j\omega T})$ on the unit circle in the complex z-plane (see Equation [2] below or FIGS. 4 and 5 in the paper by Takalo R, Hyyti H and Ihalainen H entitled "Tutorial on univariate autoregressive spectral analysis", *Journal of Clinical Monitoring and Computing,* 2005, 19, 401-410). The peaks in the frequency spectrum which correspond to each of the poles in the autoregressive model are identified. The dominant pole in the AR model can then be chosen to be the one which corresponds to the peak in the frequency spectrum with the highest magnitude.

Continuous analysis of continuous signals can be achieved by defining a time window in the representative signals, performing the spectral analysis and identification of valid information in the time window, advancing the window and repeating the analysis. For detection of physiological signals such as heart rate and breathing rate 15-second or 30-second windows respectively can be used, though they can be shorter—for example 10 seconds if the signal is of high quality. The windows can be advanced after each analysis (e.g by anything from a fraction of a second to a few seconds) to output a reading which is representative of the most recent 15 or 30 seconds.

A single measurement can be derived from the plural spatial areas by averaging the readings from them or averaging a selected number of them. The selection can be by pole magnitude, i.e. only those poles with a magnitude above a threshold, or phase angle, i.e. only those poles with a phase angle lying within a certain range, or both.

The derivation of pole magnitude and phase angle for each spatial area allows a particularly effective visual display of the detected temporal information. Thus it is possible to display the image with a display attribute of each spatial area set according to the magnitude of the dominant pole in that spatial area. For example the areas may be colour-coded. This gives a map of where valid period information is present in the image. Of course image attributes other than colour can be coded according to pole magnitude if desired.

Furthermore, the image can be displayed with a display attribute of each spatial area set according to the phase angle of the dominant pole in that spatial area. Again, colour-coding is particularly effective. This provides a map of the spectral information, for example a heart rate map or a breathing rate map over the imaged subject.

The colour (or other attribute) coding may be overlaid on the original image.

Such colour-coded maps are of considerable assistance to a clinician in judging whether or not the information being presented is valid, i.e. truly representative of the subject, or whether it is some artifact or caused by some by some other agent in the image.

The invention is therefore particularly effective for analyzing and redisplaying images which include photoplethysmogram images (PPGI) where the temporal information is at least one of heart rate and breathing rate.

The fact that the invention allows the detection of where there is valid periodic information in the image means that it also can be used to provide a particularly effective way of segmenting images. In video coding or in security applications it is often necessary to separate human or animal subjects from background and the detection of valid periodic information representative of a heart rate or breathing rate provides for an easy way of segmenting the image. Thus the image can be segmented on the basis of the magnitude of a pole, e.g. the dominant valid pole in each of the spatial areas, and/or on the basis of the phase angle of a pole, e.g. the dominant valid pole.

The invention can be implemented in a computer program or in an image analysis system. It can also be implemented in a vital sign monitor, for example, for use at home to analyses images from a standard webcam, or in a clinical setting to analyses images of a patient, for example in a critical care unit or of infants in a neonatal unit.

The invention will be further described by way of example with reference to the accompanying drawings in which:

FIG. 1A schematically illustrates a vital sign monitoring system according to an embodiment of the invention;

FIG. 1B schematically illustrates a vital sign monitoring system according to another embodiment of the invention;

FIG. 2 illustrates an example screen display to the patient in one embodiment of the invention;

FIG. 4 is a flow diagram explaining breathing rate measurement according to one embodiment of the invention;

Figure 3:
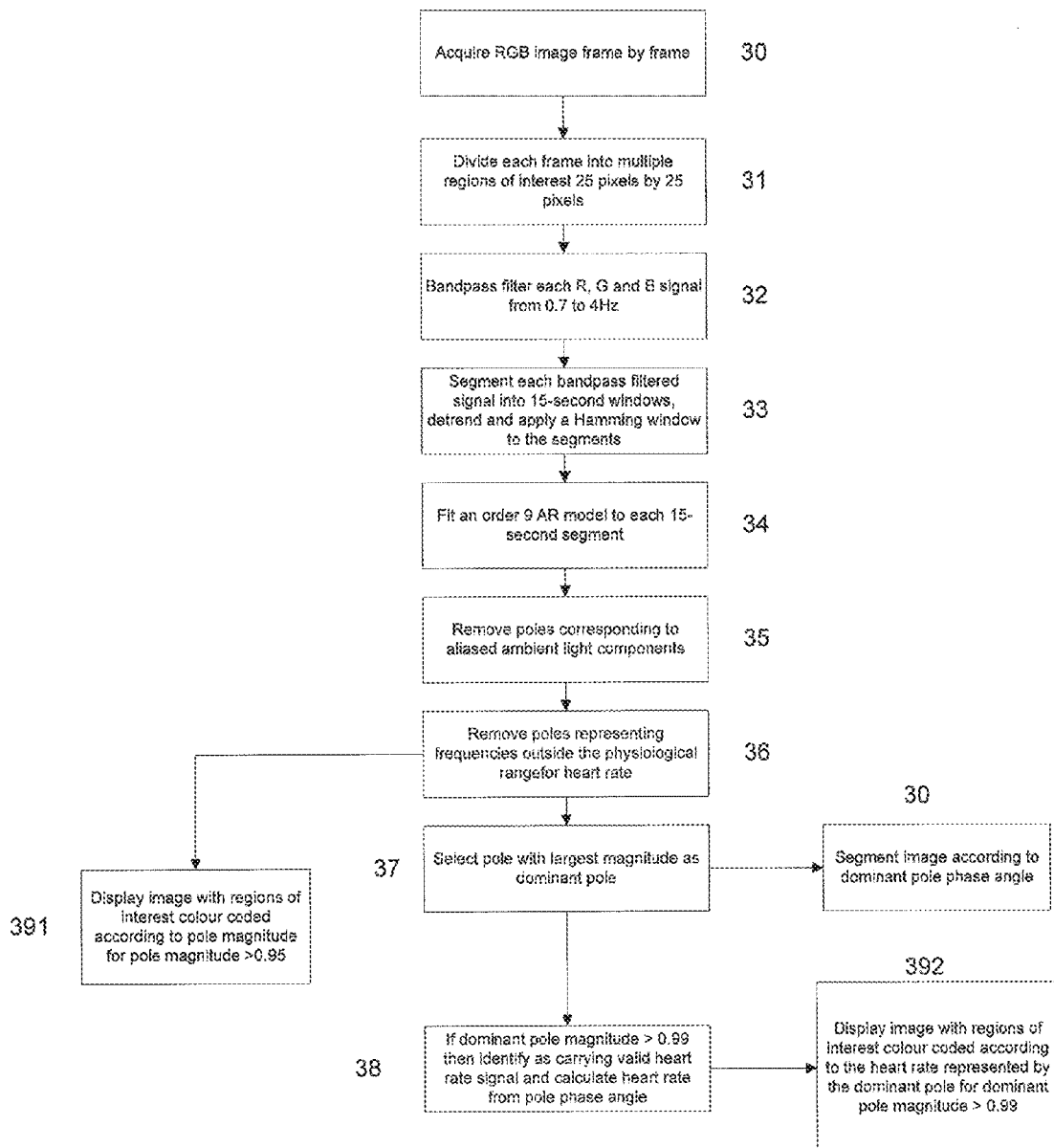
FIG. 3 is a flow diagram explaining heart rate measurement according to one embodiment of the invention.

FIGS. 5A, B and C show the first, middle and last frames of a 30 second video image sequence;

FIGS. 5D, E and F show colour-coded images of the pole magnitude, calculated heart rate and an overlay of pole magnitude on the original image respectively;

FIGS. 5G, H and I show corresponding pole magnitude, breathing rate and overlay of pole magnitude on the original image.

FIG. 1A schematically illustrates the vital sign monitoring system in accordance with one embodiment of the invention. The vital sign monitor itself is incorporated into a device 3 which has integrally provided within it a webcam 4 and screen 5. The device 3 can be a tablet or notebook computer, a mobile telephone (smartphone) or could be a television provided with a separate webcam 4. The patient 1 will be monitored by the webcam 4 while using the device 3 in their normal life, for example making a VOIP call or watching television. As will be explained below the device 3 is loaded with a software application which obtains the red, green and blue video output from the webcam 4 and analyses it to obtain vital sign measurements. These measurements are stored and displayed to the patient (on demand) and are also sent via an internet connection to a remote server 6. The remote server 6 can be accessed by a clinician's device 7 to allow a clinician to review the results and, if necessary, contact the patient either via a messaging application within the system itself or independently, for example, by telephone 9.

FIG. 1B illustrates a vital sign monitoring system in an embodiment of the invention intended for monitoring patients in hospitals. As illustrated, the vital sign monitor includes a video camera 4a mounted above the patient 1a, for example on the ceiling or a frame 17, where it can view the patient 1a while the patient is on a bed 2 or chair 8. The output from the video camera is supplied to a remote processing unit (not shown) for analyzing the video signals as explained below. A wired or wireless controller 13 may be provided to control the video camera 4a. This embodiment of the invention is particularly useful for patients who are relatively immobile, for example acutely ill in-hospital patients or infants in neonatal incubators. Such patients typically have large exposed areas of skin over which the regions of interest for the analysis can be defined.

FIG. 2 illustrates an example screen display to the patient which is associated with the software application. In this embodiment the patient is presented with five icons to select five different functions. The first icon 10 is operable when selected to launch a VOIP application and also unobtrusively to start the webcam monitoring of the patient 1 to obtain the vital-sign measurements. The icon 11 is operable when selected to start the webcam monitoring of the patient 1 to obtain the vital-sign measurements. The icon 12 is operable when selected to display a patient diary into which the patient can enter information on their condition, and again this can also unobtrusively start the webcam monitoring of the patient 1 to obtain the vital-sign measurement. The icon 14 is operable when selected to guide the patient through a self monitoring process in which the patient can use conventional devices to obtain measurements of their vital sign, for example using a Bluetooth finger probe for heart rate and oxygen saturation measurement (and breathing rate, indirectly) and a Bluetooth cuff for blood pressure measurement. Such measurements are sent to the device 3 using the Bluetooth connection and then via the internet to the server 6. Such measurements can be used to confirm the measurements obtained by analysis of the webcam video signal (e.g. if the clinician notices a deterioration in the subject's vital sign they can contact the subject to ask them to perform such a confirmation measurement). Finally the messaging icon 16 is operable when selected to start a messaging application allowing the patient to check messages received from a clinician.

FIGS. 3 and 4 set out the process for analyzing the image signals to identify regions containing valid information. FIG. 3 is particularly concerned with obtaining a valid heart rate measurement from a PPGI signal from a webcam or other video camera, and FIG. 4 with obtaining a breathing rate measurement from the same signal.

Referring to FIG. 3, in step 30 an R, G, B, image of an individual being continuously monitored is acquired frame-by-frame, for example at a 12 Hz sampling rate, by a video camera 4, 4a. The image, which typically includes the face and upper thorax, is divided in step 31 into multiple small regions, each consisting of a single pixel or multiple pixels (for example 25 by 25 pixels). Each of these regions of interest (ROI), are to be analysed for a signal representative of the subjects' heart rate and breathing rate.

To extract the heart rate information the R, G, B signals are band-pass filtered in step 32 (typically from 0.7 Hz to 4 Hz, corresponding to 42 to 240 beats/minute) and segmented into, typically, 15-second windows in step 33. The filtered values are detrended and a Hamming window is applied to each segment.

In step 34 an autoregressive model of fixed order, typically order 9, is then applied to the 15 *12 samples in the window (12 samples per second for 15 seconds).

It may be useful here to give a brief explanation of the general principles of autoregressive (AR) modeling, though AR modeling is well-known, for example in the field of speech analysis.

AR modeling can be formulated as a linear prediction problem where the current value x(n) of the signal can be modeled as a linearly weighted sum of the preceding p values. Parameter p, which is the number of samples over which the sum is taken, is the model order, which is usually much smaller than the length N of the sequence of values forming the signal. Thus:

$$x(n) = -\sum_{k=1}^{p} a_k x(n-k) + e(n) \quad (1)$$

The value of the output x(n) is therefore a linear regression on itself, with an error e(n), which is assumed to be normally distributed with zero mean and a variance of $\sigma^2$. More usefully for this application the model can alternatively be visualized in terms of a system with input e(n), and output x(n), in which case the transfer function H can be formulated as shown below:

$$H(z) = \frac{1}{\sum_{k=1}^{p} a_k z^{-k}} = \frac{z^p}{(z-z_1)(z-z_2)\ldots(z-z_p)} \quad (2)$$

where z is a complex number.

As shown in Equation 2, the denominator of H(z) can be factorised into p terms. Each of these terms defines a root $z_i$ of the denominator of H(z), corresponding to a pole of H(z). Since H(z) has no finite zeros, the AR model is an all-pole model. The poles occur in complex-conjugate pairs and define spectral peaks in the power spectrum of the signal.

They can be visualized in the complex plane as having a magnitude (distance from the origin) and phase angle (angle with the positive real axis). Higher magnitude poles correspond to higher magnitude spectral peaks and the frequency of each spectral peak is given by the phase angle of the corresponding pole. The phase angle θ corresponding to a given frequency f, is defined by Equation 3 which shows that it is also dependent on the sampling interval Δt (reciprocal of the sampling frequency):

$$\theta = 2\pi f \Delta t \quad (3)$$

Thus fitting a suitable order AR model to a signal, and obtaining the poles, reveals the spectral composition of the signal.

To find the poles, the model parameters $a_k$ are first obtained, for example using the Burg algorithm to fit the model to the signal, and from the values of $a_k$ the values of the p poles $z_1$ to $z_p$ can be calculated (see, for example, Pardey J, Roberts S, Tarassenko L, A review of parametric modeling techniques for EEG analysis, *Medical Engineering & Physics*, 1996, 18(1), 2-11). The p poles of H(z), which correspond to the p roots $z_i$ (i=1 to p) of the denominator of H(z) are found using standard mathematical procedures (for example, the MATLAB routine roots). As each pole $z_k$ can be written as a complex number $x_k+jy_k$, the frequency represented by that pole can be calculated from the phase angle of that pole in the upper half of the complex plane:

$$\theta = \tan^{-1} y/x = 2\pi f_k \cdot 1/f_s \quad (4)$$

where $f_s$ is the sampling frequency and the pole magnitude r is $(x^2+y^2)^{1/2}$.

Thus the AR model fitting of step 34 reveals the different periodic variations (spectral components) present in the image intensity signal from the region of interest.

Thus for each region of interest a set of poles is obtained, each with a given radius or magnitude up to a maximum value of 1.0 (representing the strength of that component) and a given phase angle (representing the frequency of that spectral component). Whilst these include pairs of poles corresponding to the signals of interest (e.g. the heart rate and breathing rate), AR models fitted to real, noisy, signals have multiple pairs of poles. Therefore in step 35 poles corresponding to aliased ambient light components are removed, for example by comparing the AR model from regions of interest on the subject with AR models from reference regions of interest in the background (which therefore do not include the signals of interest). Poles appearing in both the models of the background image and of the subject image (within a given angular tolerance) can be ignored. This is discussed in more detail in our copending International (PCT) patent application PCT/GB2012/052004.

In step 36 any poles outside the expected physiological range are removed and in step 37 the remaining pole with the largest magnitude is selected as the dominant pole.

In step 38 if the dominant pole in the region of interest has a magnitude greater than a predetermined threshold, for example 0.99 for a 25×25 pixel region, it is regarded as representing valid heart rate information and the heart rate it represents can be calculated from its phase angle using the expressions above.

The obtained heart rate values can be averaged, or a subset, for example the median of the top few, e.g. eleven, values can be taken.

Furthermore, as indicated in step 39 the image can be displayed with the regions of interest colour-coded according to the detected heart rate represented by the dominant pole in that region. This provides a heart rate map for the subject.

Step 391 shows an alternative display step which indicates where in the image valid periodic information is being found. This is achieved by displaying the image with regions of interest colour-coded according to the pole magnitude, preferably for poles having a magnitude greater than 0.95. This gives a map showing the location of strong periodic information in the image.

In step 392 the image can be segmented, for example to allow automatic identification of human or animal subjects in the image, by segmenting according to the magnitude or phase angle of the dominant pole in each region of interest. Effectively this means that an image can be segmented according to the presence of a valid heart rate signal in a particular region of interest. It can be used to replace image segmentation algorithms for extracting subjects in videos, or to augment such segmentation algorithms with independent information based purely on physiology.

FIG. 4 illustrates a corresponding process for obtaining breathing rate information from a PPG image. The processing is similar to that performed in FIG. 3 for heart rate extraction. In step 40 the RGB image is acquired and in step 41 it is downsampled to 2 Hz, and then in step 42 each frame is divided into regions of interest of 25 by 25 pixels. In step 43 the signals are band-pass filtered (typically from 0.1 Hz to 0.7 Hz, corresponding to 6 to 42 breaths per minute) and in step 44 they are segmented into 30-second windows, detrended and a Hamming window is applied to the segments.

In step 45 an autoregressive model of fixed order (typically 7) is then applied to the 30*2 samples in the frame and this produces a set of poles representative of the spectral components in the signal. Each pole has a particular magnitude or radius up to a maximum value of 1.0 and a phase angle representing the frequency of the spectral component. In step 46 poles corresponding to alias ambient light components are removed as described above and in step 47 any remaining poles outside the physiological range are removed. In step 48 the pole with the smallest phase angle (lowest frequency) is selected as the dominant pole provided it has a magnitude (radius) of at least 95% that of the highest-magnitude (maximum radius) pole In step 49 the breathing rate is calculated from the phase angle of the dominant pole.

A single breathing rate figure can be generated by averaging the breathing rates from the individual regions of interest, or from a subset of them, e.g. the median of the top eleven.

As indicated in steps 491 and 492 it is also possible to display colour-coded images representing the magnitude and phase angle of the dominant pole in each region, these forming maps indicating where valid breathing rate information is present in the image and also maps of the breathing rate.

In the case of the heart rate analysis and breathing rate analysis of both FIGS. 3 and 4 the 15- or 30-second windows are then moved on to select the next part of the signal and the analysis repeated. The windows may be moved on by one or more seconds each time so that the output heart rate or breathing rate is representative of the heart rate or breathing rate over the last 15 or 30 seconds respectively.

FIGS. 5A to I illustrate an example image to be analysed and the colour-coded maps generated by the embodiment of the invention above. FIGS. 5A, B and C are the first, middle and last frames of a 30 second image sequence in which the subject is a dialysis patient lying asleep on his pillow during a 4-hour dialysis session. FIG. 5D illustrates a heart rate pole magnitude map in which each 25 by 25 pixel region of interest is colour-coded according to the heart rate pole magnitude for the dominant pole, from 0.95 (minimum value—blue) to 1.0 (maximum value—red). The pole magnitude is thus a signal quality index provided directly by the autoregressive model which shows clearly where heart rate information is to be found in the image. It is clear from FIGS. 5D and F that heart rate information is to be found from most of the subject's face, apart from the eyes (which is because the subject was wearing glasses), the nose and mouth.

FIG. 5E shows the values of the heart rate for the 25 by 25 pixel regions for which the strength of the dominant pole (the signal quality index) is greater than a threshold of 0.99. The heart rate values are calculated from the phase angle of the dominant pole and colour-coded from 42 beats per minute (minimum value—blue) to 180 beats per minute (maximum value—red). FIG. 5F illustrates a combination of the pole magnitude values with the original face image to indicate the correspondence between valid information and areas of the face.

FIGS. 5G, H and I indicate corresponding maps for the breathing rate. FIG. 5G is an image obtained by colour-coding each 25 by 25 pixel region according to the pole magnitude of the dominant breathing rate pole. It can be seen that the breathing rate is to be found mostly in the upper thorax, near the nose and some of the forehead, as well as along the top of the pillow. This demonstrates that the breathing rate information in the reflected ambient light is mostly from respiration-synchronous movement, rather than intensity variations in the PPG signal. FIG. 5H is a map in which each 25 by 25 pixel region is colour-coded according to the phase angle of the dominant pole and the colour-coding scale represents the breathing rate calculated from that phase angle from 6 breaths per minute (minimum value—blue) to 42 breaths per minute (maximum value—red). FIG. 5I illustrates an overlay of the breathing rate pole magnitude values on the original face image.

With the present invention, by thresholding the signal components according to the pole magnitude, motion artifacts and other interferences are effectively discarded without having to identify them specifically. The ability to display the pole magnitude as a signal quality index on the image allows the clinician to have confidence in the values being obtained.

Although the example images in FIG. 5 are of the head and thorax of an adult patient, the invention is particularly applicable in neonatal applications where infants in incubators typically have large skin areas exposed. The invention is thus particularly effective in providing a vital sign monitor for such infant patients, especially as it does not require any contact with the patient.

PPG imaging is also of particular interest in monitoring patients in their home environments, or, for example, subjects in a clinical trial, where again the non-contact aspect of the method is particularly welcome. Providing an effective signal quality indicator is extremely useful in this field.

The specific example above refers to the analysis of an image which includes a PPG image signal. However autoregressive modeling and thresholding on the dominant pole radius as a signal quality index can be applied to other signals. For example a conventional PPG signal from a finger or ear probe can be subject to autoregressive modeling in a similar way and the dominant pole representing the strongest spectral component can be obtained. The magnitude or radius of this pole is effectively a signal quality index. Where the signal quality index has a low magnitude, it can be assumed that there is some artifact or signal dropout, and thus this signal can be ignored.

In a similar way the use of autoregressive pole radius as a signal quality index can be applied to the analysis of any noisy signal as it is an effective indicator of the loss of periodic information from the signal.

The invention may be embodied in software, for example as a software app provided on a tablet or smart phone or other mobile device, or can be incorporated into a patient monitor. Further, the signals can be analysed locally (a stand alone system) or remotely in a server-based system.

The invention claimed is:

1. A method of analysing an image of a subject to identify spatial areas which contain periodic intensity variations representing valid temporal information about the subject, comprising the steps of:
dividing said image into a plurality of spatial areas and obtaining respective signals representative of an image intensity for each spatial area;
spectrally analysing the intensity variations of each representative signal by fitting respective autoregressive models to the representative signals, each of the fitted autoregressive models comprising a plurality of poles representing spectral components of the intensity variations of each representative signal, each pole having a magnitude dependent upon the strength of the spectral component and a phase angle dependent upon the frequency of the spectral component; and
selecting those spatial areas whose fitted autoregressive model has a dominant pole whose magnitude is greater than a predetermined threshold and identifying those spatial areas as containing periodic intensity variations representing said valid temporal information.

2. A method according to claim 1 wherein the spatial areas are m by n pixels of the image where m and n are positive integers.

3. A method according to claim 1 wherein the representative signal is an average or modal intensity over the spatial area.

4. A method according to claim 1 wherein the image is a red-green-blue colour image and intensity variations in at least one of the three components are spectrally analysed.

5. A method according to claim 1 further comprising the step of identifying and ignoring poles representing spectral components outside an expected frequency range for valid temporal information.

6. A method according to claim 1 further comprising the step of identifying and ignoring poles representing ambient light intensity variations due to aliasing.

7. A method according to claim 1 further comprising the step of selecting the dominant pole as being either the pole of highest magnitude or the pole of smallest phase angle whose magnitude satisfies the threshold, and calculating from the phase angle the frequency of the intensity variation represented by the selected pole.

8. A method according to claim 7 further comprising identifying peaks in the frequency spectrum of the intensity variations and selecting as the dominant pole the pole which corresponds to the highest magnitude peak.

9. A method according to claim 1 further comprising defining a time window in each of said representative signals, performing the spectral analysis and outputting the temporal information identified as valid, advancing the window and repeating the spectral analysis and outputting the temporal information identified as valid.

10. A method according to claim 1 further comprising displaying the image with a display attribute of the spatial areas being set to represent visually the magnitude of a selected pole in the fitted autoregressive model for that spatial area.

11. A method according to claim 10 wherein:
the display attribute defines the displayed colour of each one of the spatial areas, and
the displayed colour of each one of the spatial areas is based on the magnitude of the selected pole in each one of the spatial areas.

12. A method according to claim 1 further comprising displaying the image with a display attribute of the spatial areas being set to represent visually the frequency of a pole of the fitted autoregressive model for that spatial area whose magnitude is greater than the predetermined threshold.

13. A method according to claim 12 wherein:
the display attribute defines the displayed colour of each one of the spatial areas, and
the displayed colour of each one of the spatial areas is based on the frequency of the dominant pole in each one of the spatial areas.

14. A method according to claim 1 wherein the subject is human or animal and the image contains a photoplethysmogram image.

15. A method according to claim 14 wherein the temporal information is at least one of heart rate and breathing rate.

16. A method according to claim 1 further comprising segmenting the image on the basis of at least one of the magnitude and phase angle of at least one of the poles in each of said spatial areas.

17. A non-transitory computer-readable medium comprising program code to analyse an image of a subject to identify spatial areas that contain periodic intensity variations representing valid temporal information about the subject, including:
dividing the image into a plurality of spatial areas and obtaining respective signals representative of an image intensity for each spatial area;
spectrally analysing the intensity variations of each representative signal by fitting respective autoregressive models to the representative signals, each of the fitted autoregressive models comprising a plurality of poles representing spectral components of the intensity variations of each representative signal, each pole having a magnitude dependent upon the strength of the spectral component and a phase angle dependent upon the frequency of the spectral component; and
selecting those spatial areas whose fitted autoregressive model has a dominant pole whose magnitude is greater than a predetermined threshold and identifying those spatial areas as containing periodic intensity variations representing said valid temporal information.

18. An image analysis system for analysing an image of a subject to identify spatial areas which contain periodic intensity variations representing valid temporal information about the subject, comprising:
a processor and associated memory,
wherein the memory stores computer instructions that, when executed by the processor, cause the processor to perform operations including:
dividing an image into a plurality of spatial areas and obtaining respective signals representative of an image intensity for each spatial area;
spectrally analysing the intensity variations of each resresentative signal by fitting respective autoregressive models to the representative signals, each of the fitted autoregressive models comprising a plurality of poles representing spectral components of the intensity variations of each representative signal, each pole having a magnitude dependent upon the strength of the spectral component and a phase angle dependent upon the frequency of the spectral component; and selecting those spatial areas whose fitted autoregressive model has a dominant pole whose magnitude is greater than a predetermined threshold and identifying those spatial areas as containing periodic intensity variations representing said valid temporal information.

19. A vital sign monitor comprising an image analysis system according to claim 18.

* * * * *